United States Patent [19]

Davis

[11] 4,196,615
[45] Apr. 8, 1980

[54] METHOD AND APPARATUS FOR FIELD MEASUREMENT OF INTERFACIAL TENSION BETWEEN IMMISCIBLE FLUIDS

[75] Inventor: Bruce W. Davis, Fullerton, Calif.

[73] Assignee: Chevron Research Company, San Francisco, Calif.

[21] Appl. No.: 920,584

[22] Filed: Jun. 29, 1978

[51] Int. Cl.² .............................................. G01N 13/02
[52] U.S. Cl. ..................................................... 73/64.4
[58] Field of Search ........................ 73/64.4; 324/61 R

[56] References Cited

U.S. PATENT DOCUMENTS

| 2,473,553 | 6/1949 | Stokes | 73/64.4 |
| 3,114,257 | 12/1963 | Foster et al. | 324/61 R X |
| 3,483,737 | 12/1969 | Jennings, Jr. et al. | 73/64.4 |
| 3,913,385 | 10/1975 | Jobe | 73/64.4 X |

FOREIGN PATENT DOCUMENTS 2436599  2/1976  Fed. Rep. of Germany ............ 73/64.4

OTHER PUBLICATIONS

Campbell, *Surface Tension Measurement by the Drop Weight Technique*, J. Phys. D: Appl. Phys. 3(10), pp. 1499–1504, Oct. 1070.

*Primary Examiner*—Gerald Goldberg
*Assistant Examiner*—Joseph W. Roskos
*Attorney, Agent, or Firm*—R. L. Freeland, Jr.; G. W. Wasson

[57] ABSTRACT

A tensiometer apparatus for use in the field, for instance at the site of an oil well, for measuring the interfacial tension between two immiscible fluids, for instance oil and water, wherein a droplet of one fluid is caused to move under the force of gravity through the second fluid and a characteristic of the droplet is determined by measuring the change the droplet causes in capacitance of one or more capacitors as the droplet moves through the second fluid. The determined characteristic is then converted by calibration means to interfacial tension between the fluids.

11 Claims, 2 Drawing Figures

FIG_1

METHOD AND APPARATUS FOR FIELD MEASUREMENT OF INTERFACIAL TENSION BETWEEN IMMISCIBLE FLUIDS

BACKGROUND OF THE INVENTION

This invention relates to a method and apparatus for measuring interfacial tension and, more particularly, to an apparatus which is adapted to be used in the field environment of the petroleum-producing industry.

The Problem and Its Previous Solutions

For the secondary and tertiary recovery of petroleum from subsurface reservoirs, there are several prospective processes that depend wholly or partly on the lowering of the interfacial tension between the petroleum and another liquid that is to be injected into the reservoir to push the petroleum ahead of it toward the producing wells. During the development of these prospective processes, it has already become important in laboratory work to make many measurements of the interfacial tensions between prospective pushing fluids and the particular petroleums they are proposed to push. In the future, many similar interfacial tension measurements are expected to be needed out in the oil fields themselves. For example, measurements will be needed at producing wells to determine when samples from those wells begin to show the effects of interfacial-tension lowering agents that were injected into the reservoir at distant injection wells.

Most, if not all, of the presently available instruments for measuring interfacial tension are suitable only for laboratory use. The classical instrument (usually used for determining "surface tension", i.e., interfacial tension between a liquid and a surrounding gas) is the du Nouy tensiometer, whose main working element is a small metal ring (P. Lecomte du Nuoy, G. J. Physiol. 1, 521 [1919]). The ring is suspended by a delicate wire, the plane of the ring being perpendicular to the wire and parallel to the surface of the liquid. The ring is dipped into the liquid and then pulled back out slowly. The liquid adhering to the withdrawing ring exerts a resisting downward force. Just before the liquid finally detaches itself from the ring, the part of that liquid in the immediate neighborhood of the ring has assumed the form of a right circular cylinder with a vertical axis. The final downwrd pull on the ring just before rupture is equal to the surface tension of the liquid (e.g., in dynes/cm) times twice the circumference of the ring, because the liquid cylinder has both an inside and outside surface. (For exacting work, correction terms have to be applied. See the Adamson reference cited below.)

The du Nouy tensiometer is a delicate laboratory instrument that must be used carefully. The ring that is dipped in the liquid must be chemically clean.

Other types of laboratory tensiometers have become well known. A good summary on the various types, and their relative advantages and disadvantages, appears in the book by Arthur W. Adamson, "Physical Chemistry of Surfaces", 3rd Ed., John Wiley and Sons, New York (1976), pp. 9–45.

The tensiometers closest in form to that of the present invention are the ones in which a droplet of the fluid to be tested is formed within a surrounding body of a reference fluid, and some property of that droplet is observed, a property that is relatable to the interfacial tension between the two fluids. In some tensiometers that property is the shape of the droplet, but in those most closely related to the tensiometer of the present invention, that property is the weight of the droplet. Measuring the weight of the droplets that detach from a capillary tip dates back over a century (T. Tate, Phil, Mag., 27, 176 [1864]). Correction factors for the drop weight method were worked out by Harkins and Brown (J. Am. Chem. Soc. 41, 499 [1919]). A particular variation of the drop weight method that bears on the method of the present invention was described in 1948 by Brown and McCormick (Phil. Mag. 39, 420 [1948]). They used a conical tip for forming their drops (although not a tip formed from a permeable, porous material as used in the present invention). Brown and McCormick found that the conical tip made it possible to obtain surface tensions without correcting for drop volume.

BRIEF DESCRIPTION OF THE INVENTION

The tensiometer of the present invention is one in which droplets of the fluid to be tested are formed within a surrounding body of reference fluid. They then drop through that reference fluid under the influence of gravity. However, instead of measuring the weight of the droplets after they have fallen, the present tensiometer determines their velocity of fall. The velocity of fall is relatable through Stoke's Law to the square of the droplet radius, or to the cross-sectional area of the droplet, and through known relationships taught in the above-cited references, the cross-sectional area can be related to the interfacial tension between the droplet fluid and its surrounding reference fluid. In the preferred form of the apparatus, the velocity of fall is determined by automatic detection of the droplet as it passes first one and then another of two detecting locations, the time interval between the two detections is automatically noted, and the velocity of fall is computed from that time of flight. By proper calibration, the output scale of the instrument, or the printout, may be made to read interfacial tension directly in dynes per centimeter.

In the mentioned preferred form, the automatic detection of the droplet as it passes a location is performed electrically. The detection depends on the difference between the dielectric constant of the fluid in the droplet and the dielectric constant of the surrounding reference fluid. As the droplet passes between a pair of capacitor plates whose interspace is filled with the reference fluid, the effective capacitance of the capacitor changes, and an electrical signal is produced, which in the preferred form of the invention is used as one of two similar timing signals, one for each of two detecting locations.

A variation of the invention takes advantage of the fact that in the mentioned electrical detection operation, the change in effective capacitance of the capacitor has more than just a timing aspect. The change itself has a measurable amplitude and that amplitude can be related to the size of the droplet that is passing between the capacitor plates, and the size in turn can be related to the desired interfacial tension. So it is possible to construct a form of the apparatus containing only one set of capacitor elements, rather than two sets, and in which the intermediate measured quantity is the amplitude of an electrical pulse rather than its time of occurrence.

The apparatus with a single set of capacitor elements may also be used to measure time of flight with appropriately sensitive detecting circuits that can determine from the signal derived from the capacitor the time interval between when the droplet first influences the dielectric of the capacitor until the droplet no longer influences the dielectric.

In either of the mentioned alternative forms, or others which will suggest themselves, the chief advantage of the present invention is that it makes possible a direct readout of the desired quantity—interfacial tension—and it makes possible convenient and automatic measurements under field conditions.

The objects and features of the invention will be readily apparent to those skilled in the art from the specification and appended drawings illustrating a preferred embodiment wherein:

FIG. 1 is a schematic and partially sectional view of the apparatus of the present invention, including the droplet-forming element and the sensing elements along a column; and FIG. 2 is a block diagram including the sensing elements and the signal processing circuits of the present invention.

DESCRIPTION OF THE PREFERRED EMBODIMENT

Figure 1:
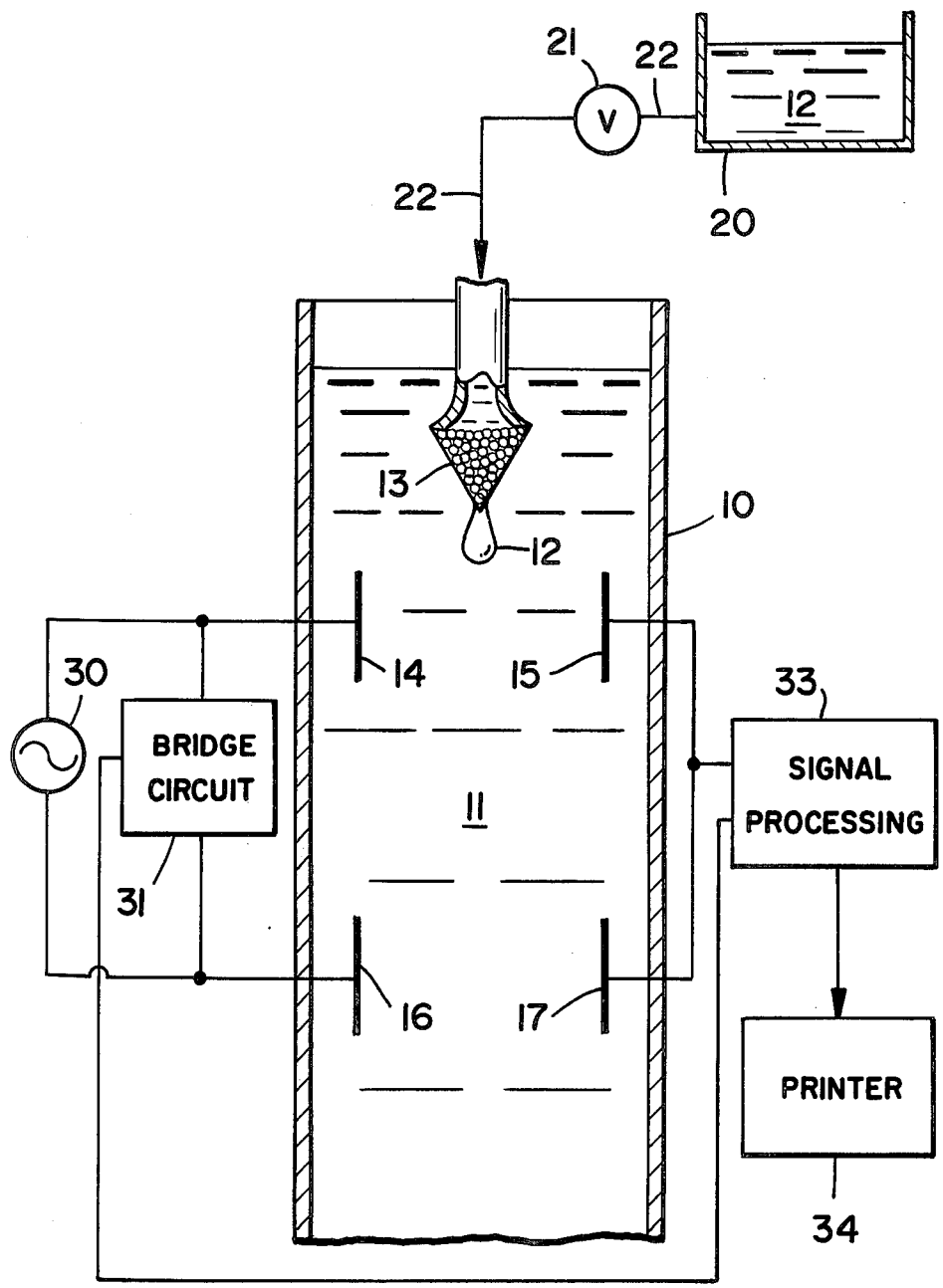

As shown in FIG. 1, a column 10 is adapted to contain a supply of reference fluid 11 into which a second fluid 12 may be introduced through a droplet-forming tip 13. The column 10 is adapted to enclose sets of capacitor plates herein illustrated as plates 14 and 15 as a set and 16 and 17 as a set.

Also shown in FIG. 1 is a container 20 for the second fluid 12 with connections through valve 21 and flow lines 22 to the tip 13 within the column 10.

Electrically connected to the sets of capacitor plates is a signal source 30 and the elements of a bridge circuit 31 which includes capacitor plates 14 and 16. Also connected to the bridge is a signal processing apparatus 33 connected to a printer 34.

It should be clearly understood that FIG. 1 is merely schematic and that the relative positions of the elements are representative only and not necessarily at the same horizontal and vertical scales. Column 10 may be substantially longer than shown and the capacitor plates will be of a size to insure detection of a signal when a droplet is present but not of a size to interfere with travel of the droplet through the tube.

Figure 2:
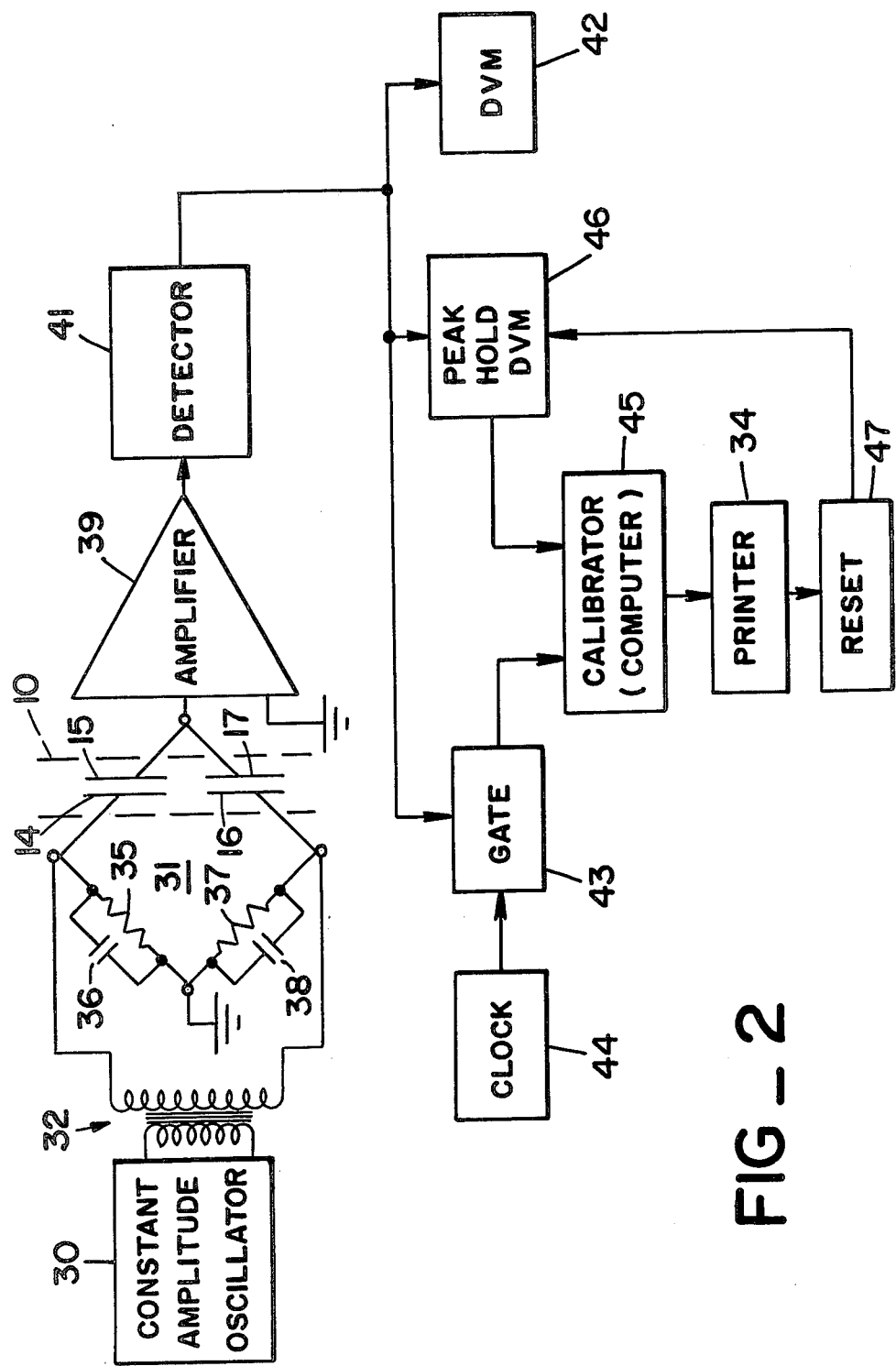

FIG. 2 is a block diagram illustrating the sensing apparatus of the present invention. As illustrated, the source 30, such as a constant amplitude oscillator, is connected through a transformer 32 to the aforementioned capacitor plates and the circuit elements of the bridge circuit 31. The bridge circuit is further constituted by branches containing resistor 35 with capacitor 36 and resistor 37 with capacitor 38. One or both of those bridge branches may include an adjustable element to produce an initial balance of the bridge 31. The other two branches of the bridge are formed by capacitor plates 14 and 15 in one branch and capacitor plates 16 and 17 in another branch. The bridge is energized from the source 30 across two of its terminals and an amplifier 39 is connected between the opposite branches of the bridge and ground in a manner to detect any changes in the balance of the bridge. Signals from the amplifier 39 are passed to detector 41 for processing to actuate the remainder of the signal processing circuits.

In the event of an unbalance in the bridge circuit 31, the output of the detector circuit 41, as will be described further hereinafter, will constitute a signal which has an amplitude proportional to the unbalance in the bridge circuit and a time dependence derived from the duration of the unbalance in the bridge. The output of the detector 41 is fed to a digital voltmeter 42, where the amplitude may be displayed.

The signals from detector 41 are also fed to a gate 43 as operating signals to open and close the gate. A timing device, such as clock 44, also supplies a signal to gate 43 so that the gate 43 functions to start and stop clock pulses as the amplifier 39 senses unbalances in the bridge circuit 31.

Gate 43 supplies output clock pulses to a calibration device such as a computer 45 where the clock pulses are converted to the desired dimensional quantities and signals representing those quantities are fed to printer 34.

The signals from the detector 41 are also supplied to a peak-hold digital voltmeter (DVM) 46 where the amplitude of the unbalance signal from the bridge 31 is held as a representation of the changes occurring in the bridge while a droplet passes between the plates of the capacitors.

A reset circuit 47 is shown connecting the printer 34 to DVM 46 to return this element to a condition to receive new signals from detector 41 as another droplet passes through the column 10.

The apparatus illustrated in FIG. 1 and the signal processing circuits of FIG. 2 are particularly adapted to the measurement of the interfacial tension between two immiscible fluids. As illustrated in FIG. 1, the column 10 is intended to contain a first reference fluid 11, through which a droplet of a second fluid 12 is passed under the influence of gravity. It should, of course, be understood that the column 10 is supported in a vertical position to provide an unobstructed vertical path for the droplet of the second fluid. It should also be understood that the reference fluid and the second fluid could have such a density relationship that the droplet of the second fluid would rise rather than fall through the reference fluid, in which case the drop forming tip 13 would be situated at the bottom of the column rather than at the top.

As shown in FIG. 1, the conical tip 13 is connected to a source of the second fluid 20 through a suitable valving system so as to produce the droplet 12. As the droplet 12 releases from the tip 13 and moves through the reference fluid, it passes between the plates 14 and 15 of a first capacitor of the bridge circuit 31 and, eventually, between plates 16 and 17 of the second branch of the bridge circuit 31. When the droplet is between the capacitor plates it displaces a volume of the reference fluid 11 and, in that way, changes the effective dielectric constant of the material between the two capacitor plates. This change in effective dielectric constant is sensed by the bridge circuit and the amount of unbalance of the bridge circuit passed to the signal processing circuit 33 is a measure of that unbalance. The amount of unbalance can be mathematically related to the diameter of the droplet 12 when it is between the two capacitor plates, and the diameter of the droplet 12 is a measure of the interfacial tension of the second fluid. The duration of time that the droplet 12 is between the capacitor plates is sensed by the bridge circuit 31 and fed through the signal processing circuits 33 to the printer 34. The length of time that the droplet of the second fluid takes to pass between two reference points can be converted to a measure of the interfacial tension between the two fluids. The diameter of the droplet of the second fluid can be determined from the length of time that it takes the fluid to pass between two different reference points and the determined diameter of the droplet can be calibrated in quantities that will represent the interfacial tension between the two fluids.

The basis for relating the interfacial tension between two fluids to the length of time that the droplet of the second fluid takes to pass between two reference points consists of two parts. First, there is a body of theoretical and experimental knowledge already referred to hereinbefore relating interfacial tension to drop weight (see especially the 1948 Brown and McCormick reference). Second, the drop weight can be related to the velocity of fall through Stokes Law (H. Lamb: "Hydrodynamics", 6th Ed., Cambridge University Press 1932,1 p. 598). Stokes Law states that the terminal velocity of a sphere moving through a viscous liquid is related to the force causing the motion by the equation:

$$F = 6\pi\mu r V_t \quad (1)$$

where:
F = force causing the motion,
$\mu$ = viscosity of the liquid surrounding the sphere,
r = radius of the sphere, and
$V_t$ = terminal velocity.

In the case of interest here, the force causing the motion is the acceleration of gravity times the virtual mass of the droplet, which is proportional to the density difference between the droplet fluid and the surrounding fluid and the volume of the droplet:

$$F = g \frac{4\pi r^3}{3} (\rho_2 - \rho_1) \quad (2)$$

where:
g = acceleration of gravity,
$\rho_2$ = density of the droplet, and
$\rho_1$ = density of the surrounding reference fluid.

Substituting the force from Equation (2) into Equation (1) gives:

$$V_t = \frac{2(\rho_2 - \rho_1)r^2 g}{9\mu} \quad (3)$$

so that the terminal velocity of the spherical droplet is proportional to its radius squared (proportional to its cross-section).

At this point, reference is made to the already cited article by Brown and McCormick (Phil. Mag. 39, 420 [1948]) on the drop weight method for determining interfacial tension. Although the symbols being used here are not identical with those of Brown and McCormick, and the following equation is not identical with any single equation of theirs, reference to their work will show that they derived the equivalent of the following equation relating interfacial tension to the squared radius of a falling drop that had been formed on a conical tip:

$$\gamma = \frac{2}{3a} r^2 (\rho_2 - \rho_1) g \quad (4)$$

where
$\gamma$ = interfacial tension, and
a = proportionality constant that is universal for all drop sizes for a given conical tip.

Dividing Equation (4) by Equation (3) gives:

$$\frac{\gamma}{V_t} = \frac{3\mu}{a} \text{ or } \gamma = \frac{3\mu}{a} V_t \quad (5)$$

That is, the interfacial tension is directly proportional to the terminal velocity, $V_t$.

Returning to the detailed description of the invention, it will now be appreciated that the proportionality constants on the right-hand side of Equation (5) can readily be taken into account in calibrator 45 of FIG. 2. So the time of flight of the droplet, first inverted to derive a velocity and then multiplied by a proportionality constant (a calibration constant) finally produces a readout of interfacial tension in dynes per centimeter, if those units are desired.

The preceding description has dealt with measurements of the time of flight of droplets moving from the interspace of one set of capacitor plates to the interface of a second set of capacitor plates. It will be apparent to those skilled in the instrumental art that a time-of-flight measurement is possible without using two sets of capacitor plates, but with only one set of plates of significant length in the direction of travel of the droplet. In the two-capacitor case, the sensing circuitry must time the interval between two similar electrical pulses, one occurring when the droplet passes the first capacitor and the other occurring when the droplet passes the second capacitor. In the single-capacitor case, the sensing circuitry must time the interval between a point on the rising edge and a point on the falling edge of the same pulse, a more prolonged pulse.

As previously described, one advantage of the apparatus of the present invention is its adaptability to use where the density and opacity of the reference fluid and the second fluid prohibit optical measurement of the desired information. As has been described, the present invention is particularly adapted to use in a field environment of a petroleum-producing operation. The column need not be optically transparent, nor need the fluids within the column be transparent, because the changes in dielectric constant and/or the time of flight for the droplet to pass between reference points is not dependent upon an optical system.

The operation of the block diagram of FIG. 2 should be readily apparent from the description of FIG. 1; however, it can be noted that the constant amplitude oscillator 30 supplies a signal across the elements of the bridge circuit 31, which includes the two RC branches in one portion of the bridge and the two capacitors in the other branches of the bridge. Across the other terminals of the bridge is the amplifier 39, which senses any changes in the capacitance of the individual capacitors made up of plates 14,15 and 16,17. Any unbalance sensed by the amplifier is supplied to the detector 41 were the amplitude of the signal is detected and the sensed unbalance is converted to timing pulses. The amplitude signal is supplied to the digital voltmeter 42 and the peak-hold DMV 46 to maintain an indication of the amplitude of the signal and the timing pulses are supplied to gate 43, where the signals are employed for initiating and terminating clock pulses. After suitable calibration, the clock pulses and the peak-hold digital voltmeter reading are supplied to the printer 34.

The calibration circuit 50 may be a computer suitably programmed to convert the amplitude signal from the peak-hold DMV to a measure of interfacial tension independently of any time of flight measurement made either with a single pair, or with two pairs, of capacitor plates. The amplitude of the unbalance detected by just one pair of capacitor plates is itself another quantity relatable to the size of the passing droplet. The theory of the relationship is too complicated to permit the derivation of an exact equation relating the size of the droplet and, in turn, the interfacial tension, to the capacitive unbalance, but an approximate relationship may be derived that shows the directional effects of all the relevant quantities, and requires only an empirical proportionality constant during final calibration.

When a droplet of relatively high dielectric constant passes between the plates of a capacitor whose interspace has been filled with a liquid of relatively low dielectric constant, the apparent dielectric constant in the interspace will be raised. The exact amount of the apparent raise would be very difficult to calculate for a capacitor whose interspace distance is comparable to the dimensions of its plates, but if "end effects" are neglected (or the electric field lines are assumed to proceed horizontally between vertical plates) a lower limit may be calculated for the apparent raise.

There is a helpful theorem to assist in the calculation, which theorem was actually stated in terms of permeabilities of a porous medium (Cardwell and Parsons, "Average Permeabilities of Heterogeneous Oil Sands", AIME TRANS. 160 [1945]34–42), but which can, by mathematical analogy, be stated here as follows: the average dielectric constant of a heterogeneous dielectric lies between the harmonic volume average and the arithmetical volume average of the actual dielectric constants in that dielectric. The lower limit is the harmonic volume average.

For the case at hand, one may write for average dielectric constant in the volume between the capacitor plates:

$$\frac{1}{\epsilon_{ave}} = \frac{\phi_1}{\epsilon_1} + \frac{\phi_2}{\epsilon_2} \qquad (6)$$

where $\epsilon_{ave}$ = the effective dielectric constant when the droplet is present,
$\epsilon_1$ = dielectric constant of the reference fluid,
$\epsilon_2$ = dielectric constant of the droplet fluid,
$\phi_1$ = volume fraction of the reference fluid (very nearly unity)
$\phi_2$ = volume fraction of the droplet fluid ($\phi_2 << 1$)

From Equation 6, $$\frac{\epsilon_1}{\epsilon_{ave}} = \phi_1 + \frac{\epsilon_1}{\epsilon_2}\phi_2 = 1 - \phi_2 + \frac{\epsilon_1}{\epsilon_2}\phi_2 \qquad (7)$$

Now, if $\epsilon_1 << \epsilon_2$, as it would be if the reference fluid were oil and the droplet fluid were water:

$$\frac{\epsilon_1}{\epsilon} \simeq 1 - \phi_2 \text{ or } \frac{\epsilon_{ave}}{\epsilon_1} \simeq 1 \text{ or } \frac{\epsilon_{ave} - \epsilon_1}{\epsilon_1} \simeq \phi_2 \qquad (8)$$

This says that the lower limit for the fractional change in the dielectric constant is equal to the fractional volume occupied by the droplet.

The apparent fractional change in the dielectric constant of the interspace is, of course, also the apparent fractional change of the respective capacitor.

Using Equation 8 for the lower limit of the fractional changes in apparent dielectric constant, and assuming an interspace of volume V, the fractional change in capacitance due to a droplet may be written:

$$\Delta C/C = K(4\pi r^3/3V) \qquad (9)$$

where K = an empirical calibration constant.

The dimensionless constant K is set into the calibrator (computer) 45.

As shown in FIG. 1, a preferred form of tip 13 for use with the field instrument is one formed from a porous sintered material. Such a tip, having many possible flow paths from its inside to its outside, is much less susceptible to plugging than a tip with only one or two flow paths such as has been used in the laboratory instruments described in the literature. A particular material that has been found to be useful is sintered stainless steel (Trinity Micro Grade E, supplied by Ball-Trinity West). Pore paths that will pass particles up to 40 microns in diameter have been found useful for droplet formation when interfacial tensions were 0.01 dyne/cm and larger. Smaller pores would be needed for lower interfacial tensions.

Throughout the specification, the fluid within the column 10 has been referred to as the reference fluid, and the fluid produced on the tip has been referred to as the second fluid. It should be readily understood that the reference fluid may be a hydrocarbon through which a second fluid of an aqueous base will pass; or, the reference fluid may be an aqueous fluid and the second fluid may be a hydrocarbon. It is, of course, essential that the two fluids be immiscible for a discrete droplet to be formed.

The apparatus of the present invention and the method for operation thereof lend themselves to an application in an oil field environment where, for instance, in the case of a surfactant flood of an oil field formation, it becomes of importance to determine when the surfactant-treated fluid has broken through to the producing well. As a surfactant breaks through with the produced fluids, the interfacial tension of the produced fluid will change, and monitoring with the present invention will show that change.

Another application for the interfacial tension meter of the present invention is to periodically fill the column 10 with produced oil that is derived from a producing well where a surfactant flood is being performed. The second fluid in this case may be droplets formed of a distilled water or brine and the interfacial tension measurement would be made with each of the different fillings of the produced oil. If a surfactant begins to break through, which has dissolved in the produced oil, then a measurable change will be detected in the interfacial tension between the droplet and the reference fluid, which change may be attributed to the surfactant entrained in the produced oil.

The techniques of the above two-described uses of the present invention may also be applied to the detection of a chemical tracer in a water-flood operation. The chemical added to the injected water may be selected so that it would not be particularly likely to absorb onto the reservoir formations, but would stay with the injected water-flood fluids. As fluids are produced at a producing well, the presence of the chemical tracer may be dectected by the changes that it will cause in the interfacial tension of the produced oils or waters.

It should be apparent from the foregoing description and the examples for its application that one of the important features of the present invention is that it produces an interfacial tension measurement of the actual fluids of interest in an oil field application and that the apparatus may be operated in the field at, for instance, the wellhead.

While certain preferred embodiments of the invention have been specifically disclosed, it should be understood that the invention is not limited thereto, as many variations will be readily apparent to those skilled in the art.

What is claimed is:

1. Apparatus for measuring the interfacial tension of immiscible fluids wherein the cross-sectional area of a drop of one of said immiscible fluids within the other is a measure of said interfacial tension, comprising:
   (1) a column containing a reference fluid;
   (2) means for producing within said reference fluid at least one discrete droplet of a second fluid, which droplet moves through said reference fluid under the influence of gravity, said droplet producing means being so constructed and arranged as to produce a droplet of a size which is dependent on the interfacial tension between said second fluid and said reference fluid and substantially independent of the configuration of said droplet producing means; and
   (3) sensing means along said column for producing a response that is a measure of the cross-sectional area of said discrete droplet.

2. The apparatus of claim 1 in which said measure of the cross-sectional area is the velocity of movement of said droplet.

3. The apparatus of claim 2 including calibration means for multiplying said measured velocity of movement by a calibration constant to derive said interfacial tension and means for producing a direct reading of said interfacial tension between said second fluid and said reference fluid.

4. The apparatus of claim 1 wherein said sensing means is a set of capacitance plates within said column along the path of movement of said droplet and means for detecting the time of flight for said droplet passing between said capacitance plates.

5. The apparatus of claim 4 wherein said sensing means includes timing means for sensing the time of flight of said droplet passing between said capacitance plates.

6. The apparatus of claim 5 wherein said sensing means includes a capacitance bridge for actuating said timing means.

7. The apparatus of claim 1 wherein said sensing means includes a set of capacitance plates within said column along the path of movement of said droplet, a capacitance bridge circuit electrically including said capacitance plates, electrical means actuated by an unbalance of said bridge circuit and including timing means for measuring the duration of said unbalance of said bridge circuit during the time of flight of said droplet between said capacitance plates, and display means for producing a visual record representative of the duration of said unbalance.

8. The apparatus of claim 1 wherein said means for producing said discrete droplet is a porous, conical tip immersed in said reference fluid and through which said second fluid is passed.

9. The apparatus of claim 8 wherein said porous, conical tip has pore paths that will pass only particles less than 40 microns in diameter.

10. A method for measuring the interfacial tension of immiscible fluids constituting a reference fluid and a second fluid, comprising the steps of:
    (1) introducing into a column containing said reference fluid at least one discrete droplet of said second fluid whereby said droplet may move under the influence of gravity through said column;
    (2) sensing the time required for said droplet of said second fluid to move a known distance through said column;
    (3) and calibrating said sensed time in terms of the cross-sectional area of said droplet to produce said measure of interfacial tension between said immiscible fluids.

11. Apparatus for measuring interfacial tension between two immiscible fluids whether or not either of said fluids is optically transparent, including
    means forming an enclosed column of one of said fluids;
    means forming a droplet of the other of said fluids within said column means, said droplet-forming means being so constructed and arranged as to form said droplet of a size which is dependent on the interfacial tension between said one of said fluids and said other of said fluids and substantially independent of the configuration of said droplet-forming means,
    electrically responsive means positioned along said column means at a predetermined distance from said droplet-forming means for detecting passage of a droplet under the influence of gravity and the difference in density of said fluids, and
    means for detecting a change in an electrical characteristic of said electrically responsive means, said change in electrical characteristic being calibratable as a measure of the interfacial tension between said fluids.

* * * * *